United States Patent [19]

Dunn

[11] Patent Number: 4,540,407
[45] Date of Patent: Sep. 10, 1985

[54] SURGICAL GLOVES AND SURFACE TREATMENT OF SURGICAL GLOVES FOR AVOIDING STARCH PERITONITIS AND THE LIKE

[76] Inventor: Robert N. Dunn, 1258 Westgate Ter., Chicago, Ill. 60607

[21] Appl. No.: 551,111

[22] Filed: Nov. 14, 1983

[51] Int. Cl.³ .............................................. A61B 19/04
[52] U.S. Cl. ....................................... 604/292; 2/168; 2/161 R
[58] Field of Search ................................. 604/292–293; 2/161 R, 168

[56] References Cited

U.S. PATENT DOCUMENTS

| | | | |
|---|---|---|---|
| 3,728,739 | 4/1973 | Semp | 2/168 |
| 4,043,344 | 8/1977 | Landi et al. | 128/1 R |
| 4,064,564 | 12/1977 | Casey | 604/292 |
| 4,291,463 | 9/1981 | Williams | 30/346.53 |
| 4,310,928 | 1/1982 | Joung | 2/161 R |

OTHER PUBLICATIONS

The Condensed Chemical Dictionary, 10th Edition, 1981, p. 825.

Primary Examiner—Stephen C. Pellegrino
Assistant Examiner—Harrie S. Samaras
Attorney, Agent, or Firm—Norman Lettvin

[57] ABSTRACT

An improved surgical glove, powdered to serve as a lubricant, is provided by using a polyol powder as the lubricant. The use of a polyol powder as the powdering agent for use on surgical gloves avoids the problem of starch peritonitis that has been reported upon in medical literature.

In one preferred application, polyol powder is dusted onto the side of the glove that will be the glove exterior, or patient-contact surface of the glove when used. Alternatively, polyol powder is dusted onto both surfaces of the glove.

2 Claims, No Drawings

SURGICAL GLOVES AND SURFACE TREATMENT OF SURGICAL GLOVES FOR AVOIDING STARCH PERITONITIS AND THE LIKE

BACKGROUND OF THE INVENTION

Surgical gloves traditionally are manufactured by providing hand-shaped molds onto which a film-forming, such as latex or other similar synthetic material, is deposited by dipping or the like. A mold-releasing powder is usually dusted first onto the mold to facilitate removal of the molded material from the mold. It is also usual pratice to apply a lubricating substance onto the outside of the molded glove, so that when the finished glove is peeled from the mold and retroverted, the interior of the glove is thus coated with a layer of lubricating powder for ease in donning the glove. Particles of the mold-releasing powder frequently remain on or entrapped in the exterior surface of the surgical glove.

Over the years, a variety of powders, including talc, have been used to dust, or coat, the inner and outer surfaces of the gloves to aid in manufacture or to provide lubrication in donning the glove. Cornstarch, or its derivatives, is presently the preferred powder agent.

Starch peritonitis, associated with the use of powders of cornstarch or its derivatives, arises as a result of residual powder particles shedding into the surgical area from the surface of a surgeon's glove into a body cavity, such as the abdomen of a person during abdominal surgery. These particles stimulate the formation of scar tissue, create adhesions, and could obstruct the bowel.

See Steinlieb, et al., "STARCH PERITONITIS AND ITS PREVENTION", *Archives of Surgery*, Vol. 112, April, 1977. Noting the problem of peritonitis flowing from use of cornstarch on or in surgeon's gloves, the authors of this report suggested the use of sodium bicarbonate as an alternative for cornstarch derivatives to lubricate the gloves. However, in solution, such as created by natural skin exudate, sodium bicarbonate would yield a slightly base solution that could be irritating to the wearer's hands.

Problems from use of cornstarch dusted surgical gloves is not limited to surgery dealing with the interior of the human body. Thus, infection has been found to occur from such glove-borne particles during optical surgery, resulting that the cornea may turn opaque. Additionally, starch can enter a surgically exposed area, through a perforation in the fingertip of a surgical glove, where the lubricating powder within the glove tends to accumulate.

Wearers of surgical gloves, such as doctors and aides, usually have been admonished to vigorously wash and wipe their surgical gloves before entering the body. Tolbert & Brown, "SURFACE POWDERS ON SURGICAL GLOVES", *Archives of Surgery*, Vol. 115, June, 1980, report their study of procedures involving talcs and other similar starch based powders which had been used as mold-releasing agents in the manufacture of surgical gloves. They report that a shedding hazard exists during surgery, even when the gloves have been previously washed and wiped, which instigates starch peritonitis and other similar complications.

One purpose of this invention is to provide a surgical glove which avoids the problems reported upon herein. Another purpose of this invention is to disclose a new method of lavage following surgery, particularly abdominal surgery.

SUMMARY OF THE INVENTION

An improved surgical glove is provided by dusting the glove with a specific polyol powder that eliminates, such as peritonitis, heretofore associated with use of certain powdered surgical gloves. The polyol powder is non-toxic and non-irritating to the body's tissues, and is readily absorbed by the human body. The specific polyol powder used is identified by its source, BASF Wyandotte Corporation, Industrial Chemicals Group, of Wyandotte, Mich. as "F-68". Entry into the body of F-68 particles, which adhered to the surgical gloves' surface during manufacture or which enter a body opening through a perforation in the surgical glove, will not create additional surgical complications. Introduction of F-68, alone in combination with other polyol powders manufactured by BASF Wyandotte Corporation, such as F-38, L101, is an aqueous/electrolytic solution or a colloidal suspension/emulsion would, therefore, appear to be a highly effective lavage for cleansing the peritoneal or thoracic body cavities.

DETAILED DESCRIPTION OF THE INVENTION

A surgical glove coated on one or both sides with a polyol powder, specifically "F-68", will provide an improved surgical glove. "F-68" is a non-ionic polyol powder, namely, poly(oxypropylene) poly(oxyethylene) polymers, manufactured and sold under the trademark "PLURONIC" by BASF Wyandotte Corporation, Wyandotte, Mich. F-68 has been reported in internal use, administered orally in animals, and is easily absorbable by animal body tissue without irritation or toxicity. Use of F-68 as a component of human plasma volume expander, or a blood fraction, ultimately suitable for intravenous administration, is disclosed in U.S. Pat. No. 3,850,903. The F-68 polyol is reported to have a molecular weight of approximately 8350, by Wyandotte publication OS-3012(765), and approximately 8750 In U.S. Pat. No. 3,850,903.

The use of polyol powder in the medical and cosmetic field has been thoroughly studied. In a toxicity study, *Pluronic Polyols . . . Toxicity and Irritation Data*, issued by BASF Wyandotte, said publication OS-3012(765), reports on two hundred eighty five (285) reported uses for polyols. None of these reported studies are directed to the use of the specific polyol, F-68, or use of any other polyol in combination with a surgical glove for purposes of avoiding infection resulting from surgery.

In carrying out the invention disclosed herein, prior to dipping a hand-shaped mold into a film-forming liquid, such as latex or other synthetic material, the mold is first dusted with a coating of F-68. When the film congeals to form a glove which is subsequently retroverted, the danger of any remaining particles on the patient-contact surfaces of the glove which could cause starch peritonitis, by falling into a body cavity, is eliminated since the F-68 polyol is bio-compatible and bioabsorbable.

Dusting this polyol powder on the glove after the glove has formed on the mold, but before retroversion during removal from the mold, results in the polyol powder being on the wearer-contact surfaces of the glove. On this surface, the polyol powder acts as a lubricant to aid in donning the glove resulting in a non-irritating solution when the polyol powder combines with natural skin exudate. The hazard of lubricant particles shedding through holes in the gloves which are foreign to the body is elminated, since the F-68 polyol is bio-compatible and non-toxic.

Tests have been performed on rats to compare the F-68 polyol powder with cornstarch. When equal amounts, by weight, of F-68 and cornstarch were deposited into the peritoneal cavity of different rats to see what reactions occurred, it was determined that the F-68 polyol powder slowly went into solution and deposited as a lubricating film onto the viscera, and did not produce any observable problem in the animal. When the cornstarch was deposited into the rat, the animal suffered a violent reaction and dense peritoneal adhesions.

This has now led applicant to conclude that an aqueous/electrolyte solution of pluronic polyol(s), or an aqueous/electrolyte colloidal suspension/emulsion containing any of F-68, F-38, L101 and/or L121, would be highly useful in cleaning out the peritoneal or thoracic body cavities following traumatic penetration, injury of a visceral structure, or any disease process, resulting inflammation or contamination of the body cavity. In addition, an aqueous/electrolyte solution or colloidal suspension/emulsion of pluronic polyol(s) would protect against the formation of adhesions (scar tissue) between viscera by coating visceral surfaces with a non-toxic lubricating film that remains following lavage. Of the polyols noted above, F-68 is water soluble, while the other polyols, F-38, L101 and L121 are less water soluble, but certainly go into suspension in an aqueous or saline electrolyte solution. There would be definite advantages in effecting lavage using F-68 polyol powder in aquenous/electrolyte solution's over use of other lavages such as a saline electrolyte solution.

While a number of forms of my invention have been described, it will be understood that the invention may be utilized in other forms and environments, so that the purpose of the appended claims is to cover all such forms of devices not disclosed but which embody the invention disclosed herein.

What is claimed and desired to be secured by Letters Patent of the United States is:

1. In a molded surgical glove that has had at least one surface thereof coated with a powder that serves either as a mold-releasing agent, or for lubricating the inside of the glove, the improvement comprising, in combination, the glove and namely F-68 powder, provided on a surface of the glove.

2. In a molded surgical glove formed that has at least one surface thereof coated with a powder, to serve either as a releasing agent for removing the molded glove from its molding form or for lubricating at least one surface of the glove to serve as a lubricating agent in donning the glove, the improvement comprising, in combination: the molded surgical glove being coated with a powder, namely F-68 provided on at least one surface of the glove, to prevent starchorigin problems, such as formation of scar tissue, adhesions, or bowel obstruction, in the patient.

* * * * *